United States Patent
Maurer et al.

(10) Patent No.: US 9,237,939 B2
(45) Date of Patent: Jan. 19, 2016

(54) HAND TOOL FOR DENTISTRY AND DENTAL PROSTHETICS

(75) Inventors: Philipp Maurer, Lucerne (CH); Matteo Taormina, Zurich (CH); Andreas Linder, Basel (CH)

(73) Assignee: Straumann Holding AG, Basel (CH)

( * ) Notice: Subject to any disclaimer, the term of this patent is extended or adjusted under 35 U.S.C. 154(b) by 1657 days.

(21) Appl. No.: 11/294,856

(22) Filed: Dec. 6, 2005

(65) Prior Publication Data
US 2006/0131906 A1    Jun. 22, 2006

(30) Foreign Application Priority Data

Dec. 7, 2004 (EP) .................................... 04028967

(51) Int. Cl.
*A61C 3/00* (2006.01)
*A61C 3/10* (2006.01)

(52) U.S. Cl.
CPC ...................... *A61C 3/10* (2013.01)

(58) Field of Classification Search
CPC .............. A61C 3/10; A61C 3/14; A61C 3/16; A61C 13/12; B23B 31/20; B23B 31/202
USPC ......... 433/146–149, 129, 153–156, 161, 162; 29/280–283, 237, 263–265; 279/2.03, 279/42, 43, 46.1–46.9, 48, 50, 51, 52, 53; 606/104; 81/453, 457, 487, 491, 7, 81/112–114, 121.1, 152; 30/329, 336; 294/87.26, 119.1, 100, 99.1, 99.2, 93, 294/86.28, 115
See application file for complete search history.

(56) References Cited

U.S. PATENT DOCUMENTS

| | | | | | |
|---|---|---|---|---|---|
| 282,606 | A | * | 8/1883 | Birch | 81/112 |
| 374,473 | A | * | 12/1887 | Jones | 301/135 |
| 633,852 | A | * | 9/1899 | Kendrick | 279/50 |
| 816,777 | A | * | 4/1906 | Brown | 81/6 |
| 855,280 | A | * | 5/1907 | Campbell | 279/50 |
| 1,876,950 | A | * | 9/1932 | Jaques | 433/154 |
| 2,026,893 | A | * | 1/1936 | Henkes | 409/126 |
| 2,389,372 | A | * | 11/1945 | Lea | 279/53 |
| 2,438,797 | A | * | 3/1948 | Bagge | 279/51 |
| 2,579,438 | A | * | 12/1951 | Longfellow | 81/453 |
| 2,619,724 | A | * | 12/1952 | Manthey et al. | 30/336 |

(Continued)

FOREIGN PATENT DOCUMENTS

| | | | |
|---|---|---|---|
| CH | 375194 A | * | 2/1964 |
| DE | 2354080 | | 7/1975 |
| FR | 2733408 | | 10/1996 |

OTHER PUBLICATIONS

English language machine translation of CH375194A, Feb. 1964.*

(Continued)

*Primary Examiner* — Yogesh Patel
(74) *Attorney, Agent, or Firm* — Novak Druce Connolly Bove + Quigg LLP

(57) ABSTRACT

A hand tool for dentistry and/or dental prosthetics, having a grip part which defines a main axis and, in the direction of the main axis, has a front end area and a read end area. The grip part has, in the front end area, an open receiving recess in which the collet element is arranged with an adjustable receiving diameter for receiving an object. The receiving diameter of the collet element can be modified by way of an actuating device. The collet element can be secured against rotation in the grip part.

5 Claims, 4 Drawing Sheets

(56) References Cited

U.S. PATENT DOCUMENTS

| | | | |
|---|---|---|---|
| 2,669,896 A | 2/1954 | Clough | |
| 2,670,963 A * | 3/1954 | Osborn | 279/53 |
| 2,684,698 A * | 7/1954 | Shaff | 81/57.42 |
| 2,752,625 A * | 7/1956 | Ponsell | 15/229.13 |
| 2,802,691 A | 8/1957 | Barr | |
| 2,833,546 A * | 5/1958 | Johnson | 279/51 |
| 3,102,565 A * | 9/1963 | Tomlin | 81/453 |
| 3,735,650 A * | 5/1973 | Weng, Jr. | 81/53.2 |
| 3,774,288 A | 11/1973 | Kuenzel | |
| 3,844,291 A * | 10/1974 | Moen | 606/206 |
| 3,918,727 A * | 11/1975 | Forsythe | 279/50 |
| 4,582,489 A * | 4/1986 | Listl | 433/102 |
| 5,213,015 A * | 5/1993 | Disston, Jr. | 81/90.9 |
| 6,415,693 B1 * | 7/2002 | Simon et al. | 81/453 |
| 2006/0048613 A1 * | 3/2006 | Abel et al. | 81/177.2 |

OTHER PUBLICATIONS

European Search Report from priority application EP04028967.0 dated May 18, 2005.

* cited by examiner

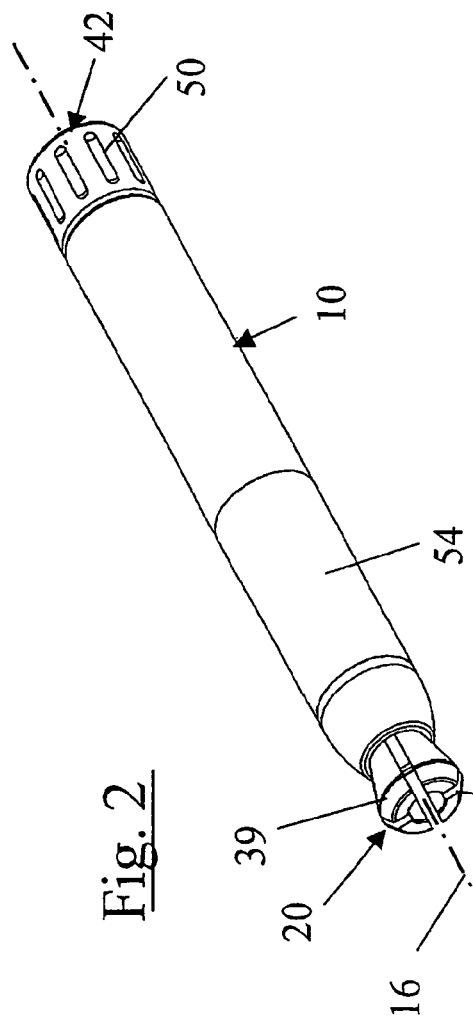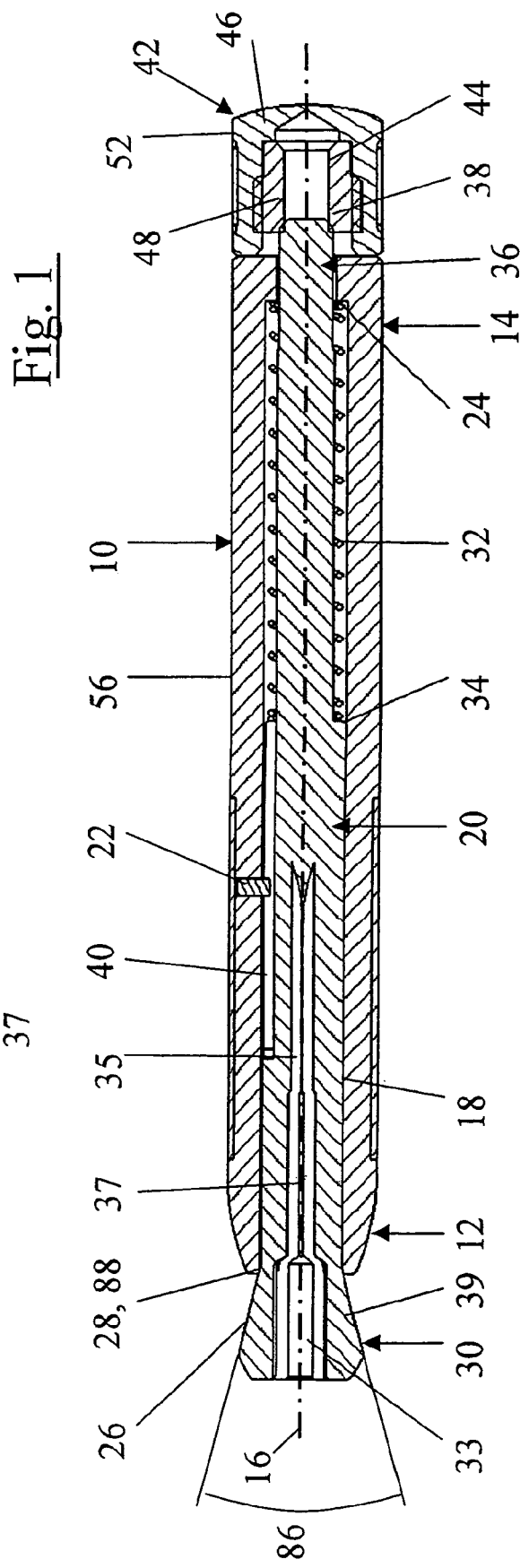

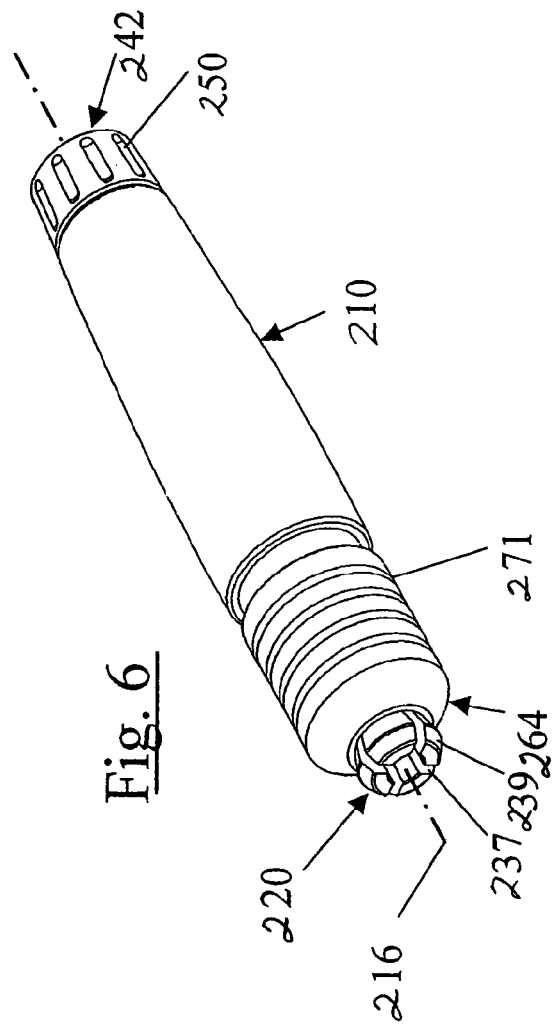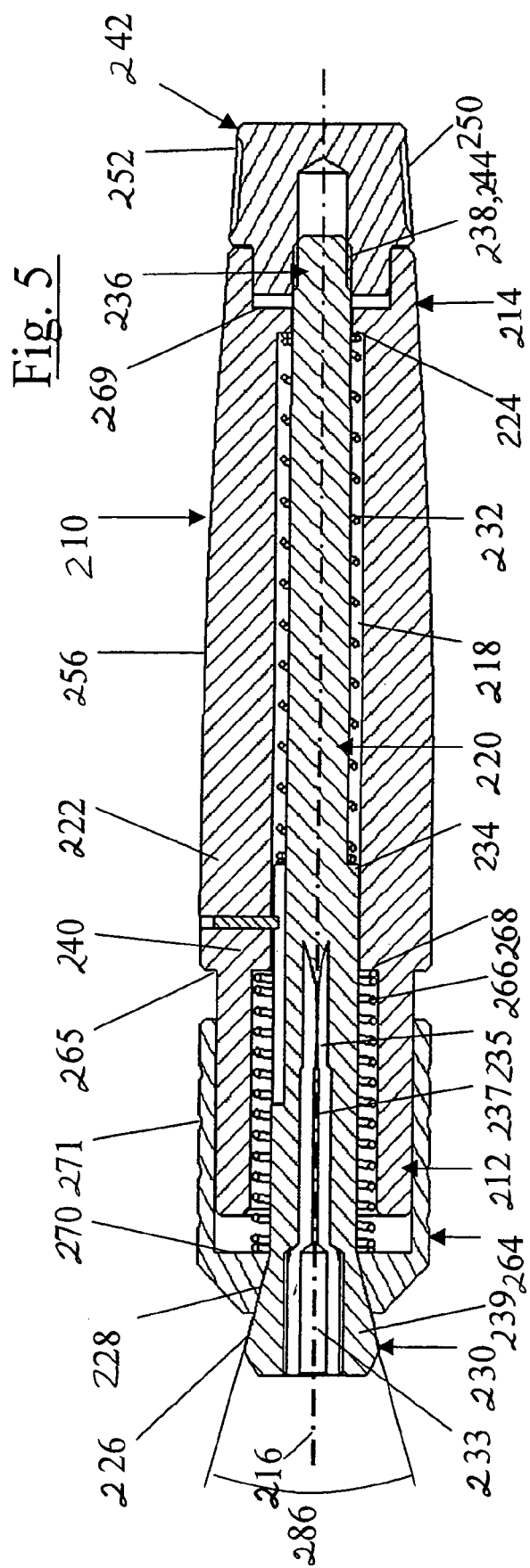

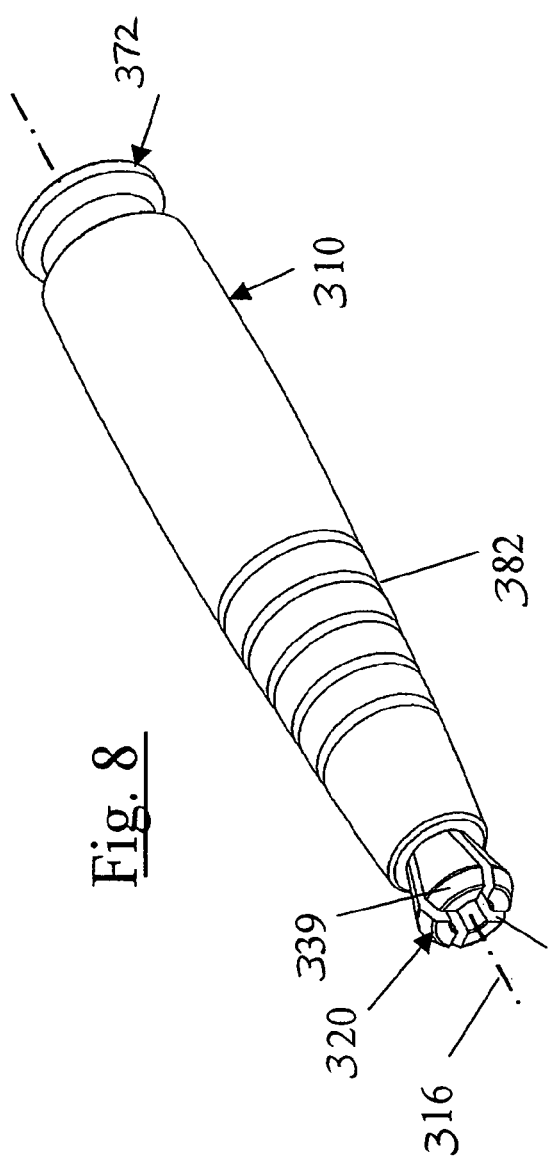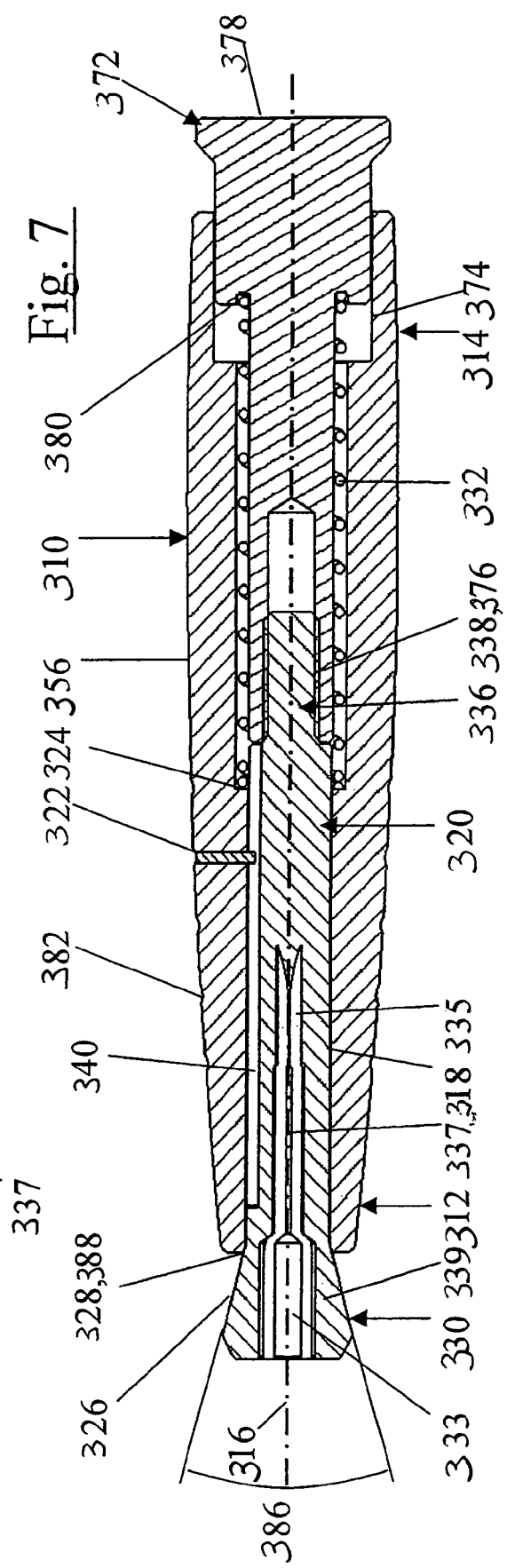

HAND TOOL FOR DENTISTRY AND DENTAL PROSTHETICS

FIELD OF THE INVENTION

The present invention relates to a hand tool for dentistry and/or dental prosthetics.

BACKGROUND

Institut Straumann AG (Basel, Switzerland) markets a hand tool for dentistry and/or dental prosthetics which is made up of a cylindrical grip part, a collet element and an actuating device, the grip part having, in the front end area, an external thread and also a receiving recess in the form of a blind bore along the main axis of the cylindrical grip part. The collet element is partially engaged in this receiving recess and is used to receive a rotationally symmetrical object that is to be worked (e.g., rotated during use). At its front end area projecting beyond the grip part, the collet element has an external cone envelope surface tapering toward the free end. The actuating device in the form of a cap-like union nut, which can be screwed on over the external thread in the front end area of the grip part, has, inside a passage, a bearing surface acting as a mating piece for the cone envelope surface of the collet element. Through this passage, the object to be clamped is introduced from the outside into the collet element completely surrounded by the union nut and the receiving recess. Because of the pressure exerted on its cone envelope surface via the bearing surface of the union nut, the collet element is pressed toward the base of the receiving recess in the grip part. A rotational movement of the union nut about the main axis, relative to the grip part, changes the pressure exerted via the support surface on the cone envelope surface of the collet element, with the result that a cylindrical recess in the clamping area of the collet element changes in diameter and the object to be worked can be clamped or released, respectively.

Since the existing hand tool is designed for working a rotationally symmetrical object, handling problems may arise if it is used on an object which is not rotationally symmetrical. The position of the object may inadvertently change during the clamping procedure.

It would thus be desirable to provide a hand tool which is easy to handle and is able to hold an object which is not rotationally symmetrical, for example a secondary element for a dental prosthesis, a dental crown or a model.

SUMMARY OF THE INVENTION

According to one embodiment of the invention, a hand tool for dentistry and/or dental prosthetics is provided having a grip part which defines a main axis and, in the direction of the main axis, comprises a front end area and a rear end area. The grip part has in the front end area an open receiving recess with a collet element arranged in the receiving recess and receiving an object. The tool further includes an actuating device for the collet element, wherein the collet element is securable against rotation in the grip part.

The collet element may be generally displaceable relative to the grip part in the direction of the main axis. The collet element may further have a longitudinal groove extending parallel to the main axis, while the grip part has a guide element which engages in the longitudinal groove to permit the securing against rotation.

The collet element may have on the outside, in a front area, a cone envelope surface which is tapering in the direction toward a rear end area of the collet element.

A spring element may be arranged in the receiving recess, one end of the spring element being directed toward the rear end area of the grip part and bearing on the grip part, and the other end of the spring element bearing on the collet element.

In one embodiment, the actuating device may have a rotary knob at the rear end area of the grip part and which bears on the grip part and is connected to the collet element via a threaded connection. When the rotary knob is turned about the main axis, the collet element is displaced in the direction of the main axis.

In another embodiment, the actuating device may have a sliding sleeve which is displaceable in the direction of the main axis and provided at the front end area of the grip part. A further spring element may be provided between the sliding sleeve and the grip part, the sliding sleeve being displaceable in the direction of the main axis.

In a further embodiment, the actuating device at the rear end area of the grip part has a push button which is connected to the collet element. A spring element is arranged in a receiving recess, one end of the spring element being directed toward the front end area of the grip part and bearing on the grip part, and the other end of the spring element bearing on the push button. When the push button is displaced in the direction of the main axis, the collet element is likewise displaced in the direction of the main axis. The push button may be connected to the collet element via a threaded connection, such that when the push button is moved in the direction of the main axis, the collet element is displaced in the direction of the main axis. When the push button is turned about the main axis, the collet element is displaced in the direction of the main axis for the purpose of presetting the cylindrical recess.

In one or more of the various embodiments described, the collet element is securable against rotation in the grip part to insure that the object to be clamped remains in a rotation position chosen by the user during a clamping procedure. The user thus faces fewer problems in the clamping operation, and handling of the tool is made much simpler.

In various embodiments, the collet element has a resilient clamping area, such as formed by clamping tongues, and the operation of the actuating element displaces the collet element relative to the grip part along the main axis. This displacement has the effect that the resilient, cylindrical receiving recess in the collet element decreases or increases in diameter in order to clamp or release the object.

In one embodiment, a simple means for securing the collet element in the grip part against rotation comprises a guide element of the grip part which engages in a longitudinal groove in the collet element, extending parallel to the main axis, to permit the securing against rotation.

In the embodiment wherein the actuating device includes a sliding sleeve movable in the direction of the main axis, it is possible to cause a more rapid change in the diameter of the cylindrical recess in the clamping area of the collet element, and consequently, a more rapid clamping or release of the object, than is possible with a rotational movement about the main axis. The rotary knob can then be used to preset the resilient clamping area of the collet element to a desired diameter of the object. Accordingly, the object is clamped or released simply through actuation of the sliding sleeve.

In another embodiment, longitudinal displacement of a push button in the end area of the grip part permits rapid and simple clamping or release of the object.

One or both of the spring element and the further spring element may comprise a helical compression spring. The use of a helical compression spring permits a simple, compact and inexpensive way of exerting a spring force in a limited space.

Further characteristics and advantages of various embodiments of the present invention will become clear from the following detailed description and drawings of illustrative examples and are not intended to limit the scope of protection of the invention.

BRIEF DESCRIPTION OF THE DRAWINGS

In the purely schematic drawings:

FIG. 1 shows a first embodiment of a hand tool according to the invention in longitudinal section;

FIG. 2 shows the first embodiment of the hand tool according to the invention in a perspective view;

FIG. 5 shows a third embodiment of a hand tool according to the invention in longitudinal section;

FIG. 6 shows the third embodiment of the hand tool according to the invention in a perspective view;

FIG. 7 shows a fourth embodiment of a hand tool according to the invention in longitudinal section; and FIG. 8 shows the fourth embodiment of the hand tool according to the invention in a perspective view.

DETAILED DESCRIPTION

Figure 4:
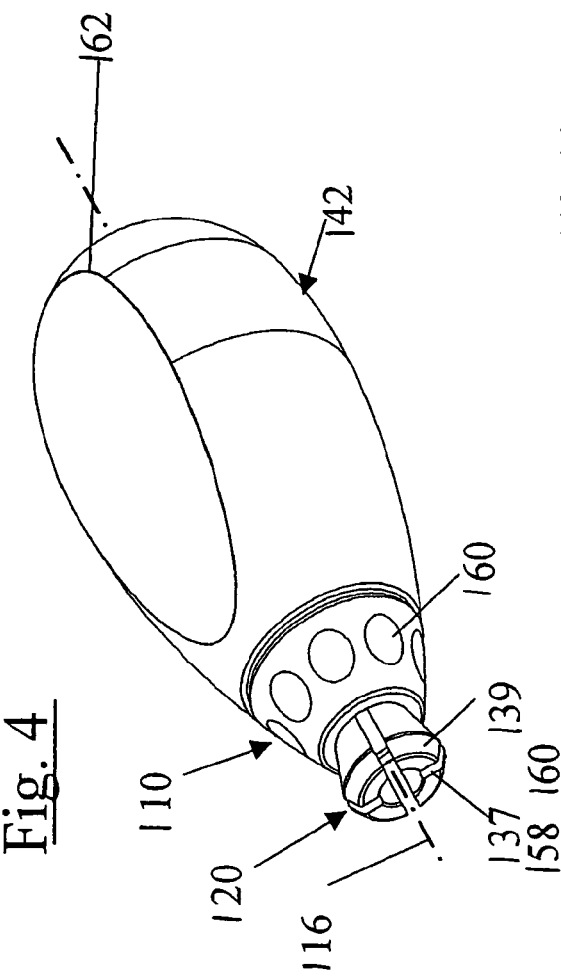
FIG. 4 shows the second embodiment of the hand tool according to the invention in a perspective view.

FIG. 1 and FIG. 2 show a first embodiment of a hand tool according to the invention in longitudinal section. A one-piece grip part 10 with a substantially circular cross section has a front end area 12 and a rear end area 14. The circular cross section defines a main axis 16. In the outer front end area 12, the cylindrical grip part 10 is rounded. For simplified and safe handling of the hand tool by the user, a rubber anti-slip element 54 in the form of a sleeve is applied on the circumferential area 56 and is arranged in that half of the hand tool directed toward the front end area 12.

In the same half of the hand tool, a pin-shaped guide element 22 in the form of a dowel pin is provided in an opening in the grip part 10 arranged radially with respect to the main axis 16, and this guide element is connected fixedly to the grip part 10.

The interior of the circular cross section of the one-piece grip part 10 is designed as a receiving recess 18 for a collet element 20. In the rear end area 14 of the grip part 10, this receiving recess 18 has a shoulder 24. The entrance area of the receiving recess 18 is located at the face of the grip part 10 in the front end area 12.

To allow the grip part 10 to act on the collet element 20, it has a bearing surface 28 in the entrance area of the receiving recess 18. In the entrance area of the receiving recess 18, the bearing surface 28 is arranged at the front opening in the front end area 12 of the grip part 10 and has a rounded configuration.

The one-piece metal collet element 20 is also substantially cylindrical and has in each case a front end area 30 and a rear end area 36. The collet element 20 also has on the outside, in its front end area 30, a cone envelope surface 26 which acts as a mating surface for the bearing surface 28 of the grip part 10 and tapers in the direction of the rear end area 36 of the collet element 20.

On the outside of the collet element 20, in the area of the guide element 22, there is a longitudinal groove 40 which is oriented in the direction of the main axis 16. This longitudinal groove 40 acts, together with the pin-shaped guide element 22 of the grip part 10, as a means for securing against rotation.

Starting from the face of the front end area 30 of the collet element 20, a recess 35 is formed in the direction of the main axis 16 and extends along about one third of the length of the collet element 20. That part of this recess 35 adjoining the face of the front end area 30 is widened as a cylindrical recess 33 approximately with the length of the cone envelope surface 26 and serves as a clamping area for the object that is to be worked. In addition, the collet element 20 has slits 37 which extend along approximately half of the collet element 20 starting from the face of the front end area 30. By means of the slits 37, clamping tongues 39 have been formed in the front end area 30 of the collet element 20, these clamping tongues having resilient characteristics.

As a support for a spring element 32, the collet element 20 has a shoulder 34 which is arranged approximately at the middle between the front end area 30 and the rear end area 36 and which faces toward the rear end area 14 of the grip part 10.

In its rear end area 36, the collet element 20 has a right-hand external thread 38 which, after assembly, protrudes from the rear end area 14 of the grip part 10.

An actuating device in the from of a multi-part, circular cylindrical rotary knob 42 is screwed onto this external thread 38. For this purpose, the rotary knob 42 has a corresponding internal thread 44. This internal thread 44 is located in a metal threaded insert 48 which is fixedly connected to a base body 46 made of plastic. The rotary knob 42 is pressed flat against the rear end area 14 of the grip part 10 by the spring element 32. For simplified and safe handling by the person using the hand tool, the base body 46 of the rotary knob 42 has depressions in the form of longitudinal grooves 50 on its outer circumference 52.

The spring element 32 in the form of a helical compression spring, which is arranged in the receiving recess 18, bears at one end on the shoulder 24 of the grip part 10 and at the other end on the shoulder 34 of the collet element 20 and engages round the collet element 20 in the direction of the main axis 16.

In FIG. 1, the collet element 20 is shown in the position in which the resilient, cylindrical recess 33 has the maximum receiving diameter.

Figure 3:
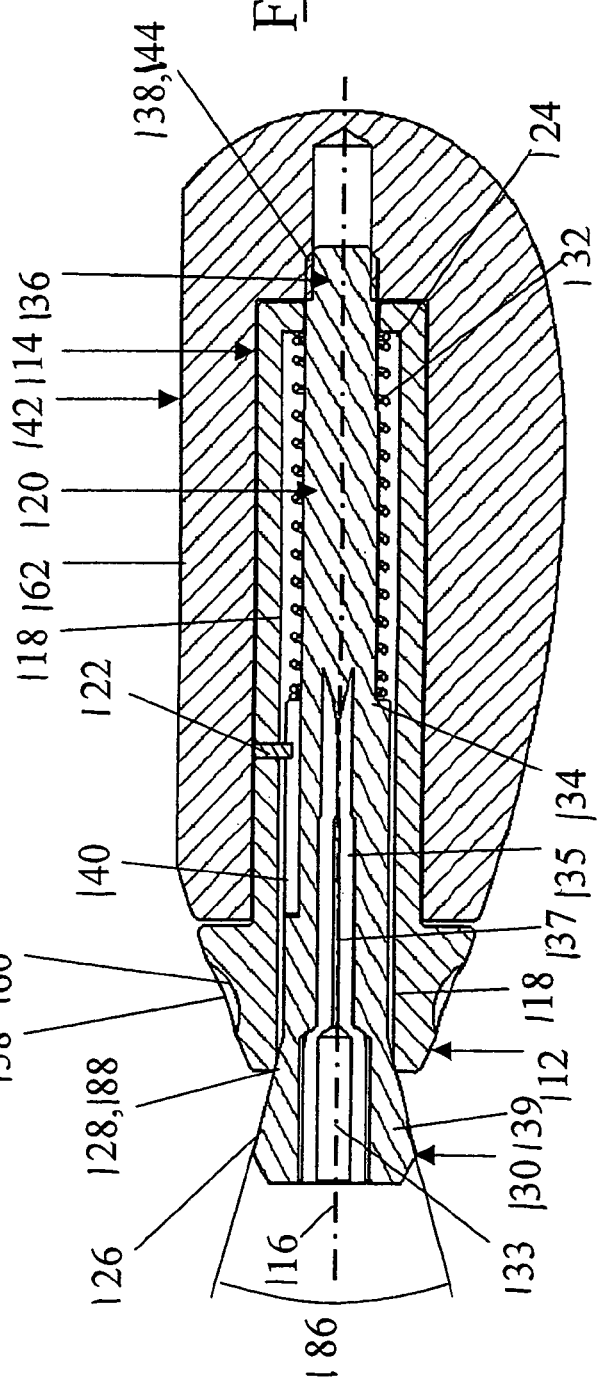
FIG. 3 shows a second embodiment of a hand tool according to the invention in longitudinal section.

FIG. 3 and FIG. 4 show a second embodiment in longitudinal section. For parts having the same action as in the first embodiment, similar reference numbers but based on a "100" number series are used below. Moreover, the second embodiment is in principle constructed like the first embodiment. Therefore, only the differences are described below.

Compared to the embodiment in FIG. 1, the grip part 110 in the front end area 112 widens in diameter on the outside. The bearing surface 128 in the entrance area of the receiving recess 118 at the opening in the front end area 112 of the grip part 110 is designed as an internal taper.

The rotary knob 142 is lengthened in the direction of the front end area 112 of the grip part 110 in such a way that it completely receives the grip part 110 except for a section 158.

For simplified and safe handling, the grip part 110 has indents 160 on the circumference of the section 158.

To make actuation of the rotary knob 142 easier, and to permit safe handling, the rotary knob 142 has a facet 162.

In FIG. 3, the collet element 120 is shown in the position in which the resilient cylindrical recess 133 has the maximum receiving diameter.

FIG. 5 and FIG. 6 show a third embodiment in longitudinal section. For parts having the same action as in the first embodiment, the same reference numbers but are based on a "200" number series are used below. Moreover, the third embodiment is in principle constructed like the first embodiment. Therefore, only the differences are described below.

Compared to the embodiment in FIG. 1, the grip part 210 is differently configured mainly in its front end area 212, because the bearing surface 228 is no longer situated in the entrance area of the receiving recess 218, but instead on a substantially cylindrical sliding sleeve 264 which, in the front end area 212, is pushed over a tapered external diameter 265 of the grip part 210. The grip part 210 also has an inner shoulder 268 in the front end area 212. In the rear end area 214, the grip part 210 has a recess 269 which axially guides the accordingly configured rotary knob 242 in the direction of the main axis 216.

The substantially hollow cylindrical sliding sleeve 264 has an end wall 270 which is located on the side of the front end area 230 of the collet element 220. The end wall 270 serves to support the spring element 232 and also as a bearing surface 228. For this purpose, the bearing surface 228 is arranged in the end wall as an internal taper which is configured to match the cone envelope surface 226 of the collet element 220. For simplified and safe operation, the sliding sleeve 264 has grooves 271 running round its circumference.

To press the sliding sleeve 264 against the cone envelope surface 226 of the collet element 220, another spring element 266 is arranged between it and the grip part 210.

The further spring element 266 in the form of a helical compression spring is arranged in the receiving recess 218 and bears at one end on the inner shoulder 268 of the grip part 220 and at the other end on the wall 270 of the sliding sleeve 264 and engages round the collet element 220 in the direction of the main axis 216.

In FIG. 5, the collet element 220 is shown in the position in which the resilient cylindrical recess 233 has the maximum receiving diameter.

FIG. 7 and FIG. 8 show a fourth embodiment in longitudinal section. For parts having the same action, the same reference numbers but based on a "300" number series are used below as were used in the first embodiment. The fourth embodiment is also constructed in principle like the first embodiment. Therefore, only the differences are described below.

Compared to the embodiment in FIG. 1, apart from having a circumferential area 356 narrowing conically toward the front end area 312 and provided with peripheral grooves 382, the grip part 310 is differently designed principally in its rear end area 314, since a push button 372 is provided here instead of the rotary knob 42.

Accordingly, the receiving recess 318 is also differently configured since, in addition to a push-button recess 374 in the rear end area 314, it again has a shoulder 324. In contrast to the first embodiment according to FIG. 1, the shoulder 324 is located approximately at the middle between the front end area 312 and the rear end area 314 of the grip part 310 and is directed toward the rear end area 314 of the grip part 310.

Similarly to the third embodiment, the push-button recess 374 serves to guide the actuating device in the direction of the main axis 316. In contrast to FIG. 3, however, instead of the rotary knob 142, the push button 372 is guided axially.

The push button 372 has an internal thread 376 oriented toward the front end area 312. This internal thread 376 is screwed onto the external thread 338 of the collet element 320. Moreover, at its free end, the push button 372 has a press surface 378 for actuating it.

The spring element 332 in the form of a helical compression spring is arranged in the receiving recess 318. In contrast to the first embodiment, it bears at one end on the shoulder 324 of the grip part 310 and at the other end on the shoulder 380 of the push button 372 and engages round the collet element 320 and also round the push button 372 in the direction of the main axis 316.

In FIG. 7, the collet element 320 is shown in the position in which the resilient cylindrical recess 333 has the maximum receiving diameter.

In all four embodiments, the collet element 20, 120, 220, 320 can be displaced relative to the grip part 10, 110, 210, 310 in a manner securable against rotation, in the direction of the main axis 16, 116, 216, 316.

In the first and second embodiments, the collet element 20, 120 is displaced in the direction of the front end area 12, 112 of the grip part 10, 110 by means of a rotational movement of the rotary knob 42, 142 in the counterclockwise sense, since the threads 38, 138 and 44, 144 are conventional right-hand threads. In this process, the cone envelope surface 26, 126 moves, in the direction of the main axis 16, 116, away from the bearing surface 28, 128 of the grip part 10, 110. With the loss of the pressure which was exerted on the cone envelope surface 26, 126 of the resilient clamping tongues 39, 139 by the bearing surface 28, 128, said resilient clamping tongues 39, 139 are freed. The result of this is that the resilient cylindrical recess 33, 133 has an increasing receiving diameter. The spring element 32, 132 presses the rotary knob 42, 142 flat against the rear end area 14, 114 of the grip part 10, 110 and thus assists the opening of the cylindrical recess 33, 133.

In the third embodiment (FIGS. 5-6), the rotary knob 242 is used to displace the collet element 220 relative to the grip part 210 in the direction of the main axis 216 in such a way that it is possible to preset the cylindrical recess 233 in accordance with the diameter of the object that is to be worked. The object that is to be worked is released by means of a longitudinal displacement of the sliding sleeve 264 along the main axis 216 in the direction of the rear end area 236 of the collet element 220. Since the spring element 232 is a compression spring, clamping takes place automatically when the sliding sleeve 264 is released.

In the fourth embodiment (FIGS. 7-8), the push button 372 serves to displace the collet element 320 relative to the grip part 310 in the direction of the main axis 316 in such a way that it is possible to preset the cylindrical recess 333 in accordance with the diameter of the object that is to be worked by turning the push button 372 about the main axis 316. The object to be worked is then clamped and released simply by a corresponding longitudinal displacement of the push button 372 in the direction of the main axis 316. The object to be worked is released by a pressing movement exerted on the push button 372 and is therefore similar to the maneuver involved in operating a conventional ballpoint pen. Since the spring element 332 is a compression spring, clamping takes place automatically when the push button 372 is released. In this embodiment, the push button 372 is connected to the collet element 320 via a threaded connection 338, 376.

It is understood that the hand tool according to the invention can hold various objects from the field of dentistry and/or dental prosthetics.

Moreover, other designs of grip part 10, 110, 210, 310, collet element 20, 120, 220, 320, rotary knob 42, 142, 242, and push button 372 are also contemplated. It is additionally understood that the individual elements, such as grip part, collet element, rotary knob, and push button, can be constructed from several parts. For example, the bearing surface 28, 128, 228, 328 in the entrance area of the receiving recess 18, 118, 218, 318, could be integrated as a separate structural component in the grip part 10, 110, 210, 310. As regards to materials, it is understood that all the parts can be made from any of various materials such as plastics, metals, sintered materials or a combination of these.

It is additionally understood that the receiving recess 18, 118, 218, 318 can be substantially conical, the cone tapering toward the rear end area 14, 114, 214, 314 of the grip part 10, 110, 210, 310.

It is also understood that the guide element 22, 122, 222, 322 can be formed directly on the grip part 10, 110, 210, 310.

In the circumferential area 56 of the grip part 10 of the hand tool according to the invention as shown in FIG. 1, an anti-slip element 54 is provided which is configured such that the operating safety is increased because the hand tool can be held better and more securely. It is conceivable that, in addition to the circumferential grooves 382 shown in FIG. 7, the grip element 310 for its part also has projections, for example stubs, and/or depressions, for example similar to the indents 160 shown in FIG. 4.

The grip element 10, 110, 210, 310 may be expediently made of a material with a good adhesion coefficient. By this means, it is possible, for example, to prevent the hand tool from accidentally slipping from the user's hand during the working of the object and/or during the clamping procedure. It is also conceivable that the grip part 10, 110, 210, 310 is coated with a layer of adhesive material. The same also applies equally to the actuating elements, namely rotary knob 42, 142, 242, push button 372, and sliding sleeve 264.

Since the object that is to be worked may become very hot during the working operation, heat conduction may also cause the front end area 12, 112, 212, 312 of the grip part 10, 110, 210, 310 in particular, and also the sliding sleeve 264, to heat up too. It is possible, however, to ensure that the fingers of the person using the hand tool according to the invention are protected from undesired effects of heat. Particularly in cases where the collet element 20, 120, 220, 320 is made of metal, it is recommended to thermally insulate the circumferential area 56, 156, 256, 356 of the grip part 10, 110, 210, 310, and also to thermally insulate the sliding sleeve 264. A desired thermal insulation can be obtained, for example, by using nonmetallic, thermally insulating materials for the grip part 10, 110, 210, 310, for any anti-slip elements 54, and for the sliding sleeve 264. It is likewise contemplated to achieve this by means of a multi-part, thermally insulating construction of the grip part 10, 110, 210, 310 and of the sliding sleeve 264, where those parts that have to be touched directly by the user are advantageously made from plastic. The proposed solution for thermal insulation also applies equally to the rotary knob 42, 142, 242, and the push button 372.

The difference in diameter of the cylindrical recess when opened derives from the geometry of the collet element. A greater difference in opening of the cylindrical recess 33, 133, 233, 333 of the collet element 20, 120, 220, 320 can be achieved, first, by the displacement of the collet element relative to the grip part 10, 110, 210, 320 in the direction of the front end area 12, 112, 212, 312 of the grip part along the main axis 16, 116, 216, 316 and, secondly, by a greater cone angle 86, 186, 286, 386. Instead of the hitherto customary cone angle of the cone envelope surface in the front end area of the collet element of about 20° to 30°, the cone angle of the cone envelope surface 26, 126, 226, 326 in the front end area 30, 130, 320, 330 of the collet element of the hand tool according to the invention is considerably greater at 40° to about 100°.

The effect of this is as follows. By virtue of the greater cone angle 86, 186, 286, 386 of the cone envelope surface 26, 126, 226, 326 the difference in opening of the cylindrical recess 33, 133, 233, 333 changes more in diameter compared to the hitherto customary cone angle, while the displacement in the direction of the main axis 16, 116, 216, 316 remains the same. Therefore, in the hand tool according to the invention, an opening difference and thus a clamping area of about 2 to about 5 mm in diameter can be achieved, whereas, in the prior customary hand tool, only an opening difference of about 1 mm in diameter is attainable. The clamping area of the hand tool according to the invention consequently permits clamping of objects with more different diameters than is the case with the prior customary hand tool.

It is also contemplated that the connection of the rotary knob 42, 142, 242 or push button 372, to the collet element 20, 120, 220, 320 is designed as a snap-fit closure. In this case, the snap-fit connection can be made releasable or nonreleasable. It is also possible for one or more intermediate pieces to be located between the collet element 20, 120, 220, 320 and the rotary knob 42, 142, 242 or push button 372. In the case of a connection in the form of a threaded connection, it is likewise possible that the collet element, instead of having an external thread 38, 138, 238 has an internal thread into which it is possible to screw a threaded pin, with corresponding external thread, connected to the rotary knob 42, 142, 242 or push button 372. It is further contemplated that adhesion means in the threaded connection prevent accidental release of the threaded connection and thus ensure that the individual parts of the hand tool according to the invention are not mislaid. Of course, it is also possible that the threads are multiple threads.

It is also contemplated that the hand tool provides the actuating elements (such as rotary knob 42, 142, 242 and push button 372) that cannot readily be removed. This can afford advantages in terms of preventing loss of the individual parts of the hand tool.

The invention claimed is:

1. A hand tool for dentistry and/or dental prosthetics, comprising:
    a grip part having an open receiving recess along a main axis, wherein the grip part is made to be gripped by hand;
    an actuating device having a sliding sleeve displaceable in the direction of the main axis and provided at the front end area of the grip part; and
    a collet element disposed in the receiving recess of the grip part, the collet element having an adjustable receiving diameter and configured to receive an object;
    the grip part having a front end area and a rear end area, the grip part including:
        a guide element configured to secure the collet element against rotation within the grip part, and
        a bearing surface provided on the sliding sleeve, and
        a first spring element provided in the receiving recess between the sliding sleeve and the grip part to engage the collet, one end of the first spring element bearing on an inner shoulder of the grip part and the other end bearing on an end wall of the sliding sleeve,
    the collet element has a longitudinal groove in an outer surface of the collet element extending parallel to the main axis between the collet element and the grip part,
    the guide element is configured to engage in the longitudinal groove to allow axial movement of the collet element in the receiving recess while the guide element is fixed to the grip part, and to secure the collet element against rotation in the grip part such that an object to be received by the collet element remains in a predetermined rotation position,
    the collet element has a cone envelope surface that extends from the front end area and is configured to mate with the bearing surface of the grip part, the cone envelope surface tapers linearly in the direction of the rear end area of the collet element, the rate of taper of the cone envelope surface defining a cone angle of 40° to 100°, the actuating device is configured to adjust the receiving diameter of the collet element, the actuating device includes a rotary knob configured to engage the rear end area of the grip part and which is connectable to the collet element via a threaded connection, and a second spring element is provided in the receiving recess, one end of the second spring element bearing on the grip part at the rear end area of the grip part, and the other end bearing on the collet element, such that when the second spring element is compressed the rotary knob is pressed against the rear end area of the grip part and the collet element is retracted in the receiving recess, and when the rotary knob is rotated about the main axis in a first direction the second spring element is relaxed to move the collet element in the direction of the front end area of the grip part.

2. The hand tool of claim 1, wherein the first spring element and the second spring element each comprise a helical compression spring.

3. The hand tool of claim 1, wherein the bearing surface is configured to match the cone envelope surface of the collet element.

4. The hand tool of claim 1, wherein the collet element is configured to receive an object that is not rotationally symmetrical.

5. The hand tool of claim 4, wherein the object the collet element is configured to receive is at least one of an element for a dental prosthesis, a dental crown, and a model.

* * * * *